United States Patent [19]

May et al.

[11] Patent Number: 4,938,602

[45] Date of Patent: Jul. 3, 1990

[54] AUTOMATED PROCESS MONITORING

[75] Inventors: Joe T. May; Edward A. Casacia, both of Leesburg, Va.

[73] Assignee: Electronic Instrumentation and Technology, Inc., Sterling, Va.

[21] Appl. No.: 329,293

[22] Filed: Mar. 27, 1989

Related U.S. Application Data

[63] Continuation-in-part of Ser. No. 108,693, Oct. 15, 1987, abandoned.

[51] Int. Cl.⁵ .............................................. G01N 21/85
[52] U.S. Cl. ..................................... 356/435; 356/436
[58] Field of Search ............... 356/432, 433, 435, 436, 356/440, 442; 354/298, 324

[56] References Cited

U.S. PATENT DOCUMENTS

| | | | |
|---|---|---|---|
| 3,398,023 | 8/1968 | Jacobsen et al. | 350/584 |
| 3,851,976 | 12/1974 | Meier | 356/442 |
| 3,918,815 | 11/1975 | Gadbois | 356/435 |
| 4,119,989 | 10/1978 | Carvalko et al. | 354/298 |
| 4,124,301 | 11/1978 | Pocock | 356/432 |
| 4,132,585 | 1/1979 | Oxford | 356/442 |
| 4,166,702 | 9/1979 | Okamoto et al. | 356/440 |
| 4,544,273 | 10/1985 | Berndt | 356/434 |
| 4,637,730 | 1/1987 | Ponstingl et al. | 356/411 |

Primary Examiner—Richard A. Rosenberger
Attorney, Agent, or Firm—Whitham & Marhoefer

[57] ABSTRACT

Instrumentation for measuring the amount of material dissolved in a liquid solution which utilizes electro-optic technology based on the Beer-Lambert Law is implemented either as a portable, battery powered model or integrated in an automated process monitoring system. In the portable, battery powered model, a sample probe (14) is inserted into a solution to be measured. The results of the measurement are displayed on a display (22). The displayed results are frozen for a predetermined period of time at the expiration of which, the power is turned off to conserve battery power. In the automated process monitoring model, a solution loading analyzer (100) is supplied with a sample of solution to be analyzed. A probe (14) positioned in a measurement well (200) is used to determine the ratio of incident light to light transmitted through the sample. A spray nozzle (212) is used for cleaning the probe head (16).

20 Claims, 7 Drawing Sheets

FIG.6  MEASUREMENT RESULTS, KNOWN CONCENTRATIONS

FIG.7  DEVELOPING TIME VERSUS LOADING

FIG. 8

AUTOMATED PROCESS MONITORING

CROSS-REFERENCE TO RELATED APPLICATION

This application is a continuation-in-part of co-pending application Ser. No. 07/108,693, filed Oct. 15, 1987, now abandoned.

BACKGROUND OF THE INVENTION

1. Field of the Invention

The invention generally relates to chemical analysis instruments and, more particularly, to devices for monitoring the amount of material dissolved in a liquid solution.

2. Description of the Prior Art

Proper determination of the amount of material dissolved in a liquid is a problem frequently encountered in chemical processing facilities. For example, in the printed circuit board industry there is a need to know the amount of photoresist dissolved in a developer or stripper bath for replacement or replenishment purposes, in waste water management facilities there is a need to know the amount of dissolved solids in water effluent to satisfy health code regulations, in an electroplating operation there is a need to know the clarity of solution because it is an indication of the amount of plating chemical in solution. Other chemical processing facilities have similar solution monitoring requirements. Visual estimation is inaccurate at best and totally wrong at worst. Laboratory determination of the percentage of dissolved solids is inconvenient, time consuming and expensive. However, the penalty for having too much or too little material in a solution can be serious.

Currently, an emphasis has been placed on fully automating chemical processing facilities. Decreased human involvement can reduce costs and improve plant safety. For example, in the printed circuit manufacturing business, the operation of printed circuit printers can be improved by monitoring systems which provide automatic checks on the developer and stripper baths. Printed circuit printing involves the use of photoresist material for various operations. Photoresist which is exposed to ultraviolet (UV) energy is polymerized and is removed from the printed circuit substrate or laminate with a stripper solution (typically, sodium hydroxide). Photoresist which is protected from UV induced polymerization is removed from the printed circuit substrate or laminate with a developer solution (typically, 1-2% sodium carbonate). In both developing and stripping, the developer or stripper solution is sprayed over the substrate or laminate and the photoresist enters semi-solution in the developer or stripper bath, respectively. Photoresist collecting in the developer or stripper baths is called "solution loading".

Proper use of developer and stripper solutions is a compromise between the volume of developer and stripper solutions used and the cleanliness of the developer and stripper solutions. It would be desirable to use perfectly clean developer and stripper solutions for each substrate being patterned; however, large amounts of waste developer and stripper would be produced if clean developer and stripper was used for every substrate. Operating costs are increased by the added cost of proper treatment of waste developer and stripper. Allowing the developer or stripper solution to dissolve excessive amounts of photoresist ultimately results in very slow or improper developing or stripping. Improper development may lead to between-trace shorts which render the printed circuit produced useless.

In prior art printed circuit printers, the following methods for changing or replenishing developer and stripper solutions have been used: (1) the solution is changed routinely on a fixed time schedule, such as once per day, (2) the board area processed is estimated and replenishment or replacement is implemented when solution loading approaches a predetermined level, (3) samples are evaluated in a chemistry lab on a regular basis and replenishment or replacement occurs when loading approaches a predetermined level, and (4) the solution pH is measured and replenishment or replacement occurs when the pH drops below a predetermined level. None of these approaches has provided totally satisfactory results. In methods (1) and (2), replenishing or replacing the solution occurs without testing the solution; therefore, it is not possible to determine whether a proper compromise between the volume of developer or stripper used and the cleanliness of the developer or stripper has been reached. Method (3) requires personnel to periodically dip a sample cup into the bath and then analyze the level of photoresist solids in the sample. In addition to the salaries required for trained personnel and costs associated with testing instruments such as spectrophotometers, periodic sampling has the additional disadvantages of being too time consuming to accommodate the quick and easy results demanded in a production environment and of putting too much reliance on the personnel to take the samples at properly timed intervals. Only method (4), measurements based on pH, is compatible with automated operation; however, because of various technical problems, results using pH as a guide have not been very satisfactory.

Printed circuit printers use medium intensity ultraviolet (UV) lamps for imaging a substrate clad with photoresist. Proper exposure of the photoresist is very important to overall process quality. UV integrators equipped with silicon photodetector UV sensors control the amount of UV energy which is directed upon the photoresist. In present day printed circuit printers, the UV integrator and associated sensor are used continuously during normal operation. Sensors have been found to experience long term degradation due to prolonged exposure to UV energy (a phenomena called "solarization"). The integrator circuitry itself is also subject to drift and occasional failure.

SUMMARY OF THE INVENTION

It is therefore an object of the invention to provide an instrument capable of the direct measurement of the amount of material dissolved in a solution.

It is another object of the invention to provide an instrument which can be used in a production environment for making direct readings of the amount of material dissolved in a solution.

It is another object of the invention to provide an instrument for making direct measurements of the amount of material dissolved in a solution which can take the form of a hand held, battery powered instrument or a continuous, in-line instrument.

It is yet another object of this invention to provide for improved automated processing of printed circuit boards by monitoring the UV imaging and developer loading processes.

According to the invention, electro-optic technology has been utilized to produce an instrument which can measure the amount of material dissolved in a liquid solution. The operating principles of the instrument are based on the Beer-Lambert Law which states that the optical absorbance of a solution is proportional to the concentration of the material dissolved in it. A light of selected wavelength is passed through the solution to be analyzed. A photodetector senses the amount of light passing through the solution, and electronic circuitry performs the necessary computations to calculate optical absorbance and associated concentration.

The instrument may take the form of a rugged and portable battery powered instrument. A ruggedized sample probe is inserted in a solution to be measured. The optical absorbance across a channel in the probe head is measured using light radiating and light sensing devices positioned on either side of the channel in the probe head. The intensity of incident light is measured by a first sensor while the intensity of light which passed through the solution present in the probe head channel is measured by a second sensor. Electronic circuitry uses the signals produced by the first and second sensors to compute absorbance. The results of the measurement are displayed on a large readout, such as a liquid crystal display (LCD). The instrument can be precalibrated to measure several different liquids. Calibration is simple and requires no training.

The instrument may be implemented in an automated process monitoring environment where samples are automatically tested at timed intervals. For example, in a printed circuit printer the solution loading in the developer and stripper baths can be monitored by withdrawing a sample from a bath at timed intervals, sending the sample to a testing chamber, de-aerating the sample, measuring the optical absorbance of the sample, returning the sample to the bath, and cleaning the probe head. The optical absorbance of the sample can be measured using a probe head, as described above with regard to the portable battery powered unit, positioned in the testing chamber. Upon detecting an unfavorable amount of developer or stripper loading, the developer or stripper is either replenished or replaced. The entire operation can be performed under the direction of a programmable logic controller.

The printed circuit printer implementation of the invention is but one example of automated process monitoring. In a waste water management plant where the amount of dissolved solids present in the water is subject to health regulations, the instrument can be implemented to test the effluent at required intervals. Precalibrating would be accomplished by zeroing on clear water and then adjusting a SPAN potentiometer to read the concentration of a known sample of waste water. In an industrial fermenter, the concentration of dissolved solids can be monitored. In an electroplating operation, the clarity of the solution in the electroplating bath can be measured as an indication of an amount of plating chemical in the solution. The instrument can be set up for automatic process monitoring of almost any chemical process. All that is required is proper calibration of the instrument for the solution to be monitored. The advantage of the automated process arrangement is in eliminating the requirement of having personnel perform the necessary measurements.

The programmable logic controller in a printed circuit printer with automated process monitoring may also routinely check the operation of the imager by periodically comparing the output of the working sensor against a reference sensor to detect the effects of solarization. The output of a UV sensor is a current proportional to UV light intensity. By periodically opening a shutter, a reference sensor is temporarily exposed to the same intensity of UV energy as the working sensor. The reference sensor is only exposed to the UV light for a short time so that it does suffer the same solarization effects as the working sensor which is continuously exposed. The currents emanating from both sensors are compared to determine whether the working sensor is operating correctly.

BRIEF DESCRIPTION OF THE DRAWINGS

The foregoing and other objects, aspects and advantages of the invention will be better appreciated from the following detailed description of the preferred embodiments of the invention with reference to the drawings, in which.

DETAILED DESCRIPTION OF THE PREFERRED EMBODIMENTS OF THE INVENTION

Figure 1:
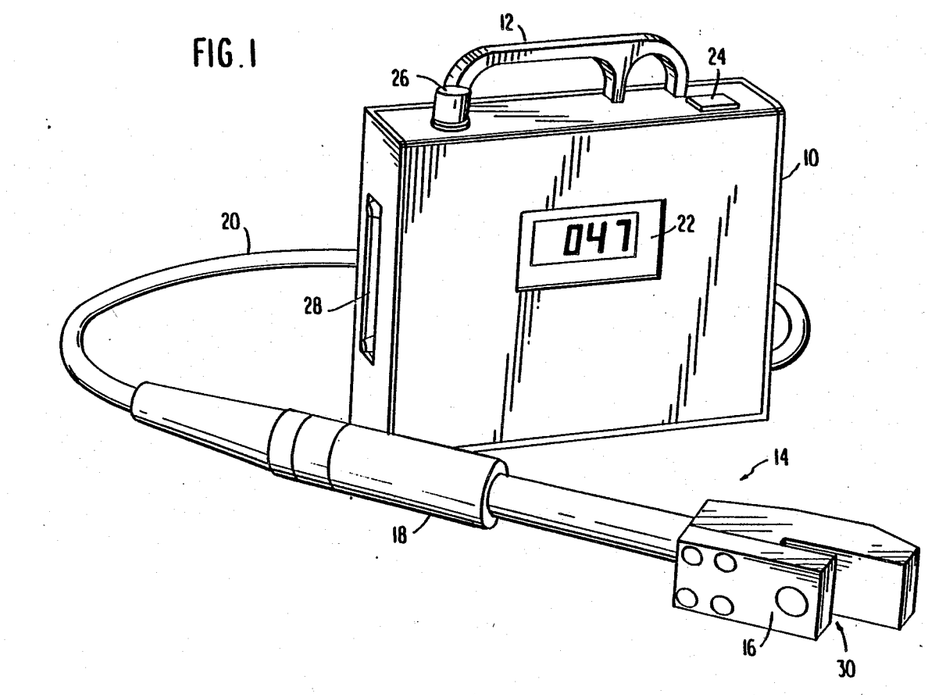
FIG. 1 is a pictorial illustration of a portable, battery powered solution loading analyzer.

Referring now to the drawings, and more particularly to FIG. 1, there is shown a solution loading analyzer comprising a case or housing 10 with a carrying handle 12 and an attached probe 14. The probe 14 is composed of a probe head 16, a handle 18 and a cable connected between the handle 18 and the housing 10. The probe head 16 and handle 18 may be comprised of polypropylene with VYCOR optical windows and silicone rubber window seals; however, the materials employed are chosen according to the type of solutions to be analyzed and the conditions under which analysis will be performed. The entire probe 14, including the cable 20, can survive complete immersion in most caustic industrial solutions for short periods. The probe is also mechanically rugged and can generally survive being dropped on a hard surface.

The housing has on one face thereof a digital display 22, which can be an LCD. On the top of the housing 10, adjacent one end of the handle 12, is a push button switch 24, while adjacent the other end of the handle 12 is a rotary switch 26. On one side of the housing 10 is an access panel 28 which may be opened to reveal screw driver adjustments for potentiometers used to precalibrate the instrument.

In operation, the probe 14 is held in the operator's right hand and inserted into the solution to be measured. Testing is initiated by depressing push button switch 24. This may be done with the thumb of the left hand which grasps the handle 12. The measurement is made automatically and the result is displayed in digital form on the display 22, in appropriate units such as ft$^2$-mil/gal, gram-moles/liter, % loaded, etc. Three separate calibration settings are available by means of rotary switch 26 so that up to three different solutions may be measured with a single instrument.

The operating principles are based on the Beer-Lambert Law which, by convention, is expressed by the following equation:

$$\text{Log}_{10}(I/I_o) = -\epsilon c x$$

where I is the intensity of the light through the sample, $I_o$ is the intensity of the incident light, $\epsilon$ is a proportionality constant, c is the concentration of material in solution, and x is the thickness of the absorber. Absorption, A, is described quantitatively as the log of the ratio of measured light to incident light as expressed in the following equation:

$$A = -\log(I/I_o) = +\epsilon c x$$

In the subject invention, light of a selected wavelength is passed through the solution which fills a gap 30 in the probe head 16. A photodetector senses the amount of light passing through the solution, and electronic circuitry, shown in FIG. 2, within the housing 10 compares the transmitted value of light with the incident value. Analog circuitry performs the necessary computations to calculate the optical absorbance and associated concentration. The result is converted to a digital form and displayed in appropriate units on display 22.

Calibration is simple. During calibration, the sample probe 14 is inserted in a solution which contains no dissolved material. The solution does not have to be visually clear. A ZERO potentiometer is adjusted to provide a zero reading on the display 22. The probe 14 is then inserted into a solution of known concentration. A corresponding SPAN potentiometer is adjusted to provide the value of the known concentration on the digital display 22. This procedure is repeated for each different solution for which the instrument is to be precalibrated. Presently, the hand held instrument can be precalibrated for three different solutions.

As mentioned, the portable instrument shown in FIG. 1 is battery powered. A low battery warning feature activates the display 22 with a "LO BAT" indication when battery charge is less than 10% of the full charge. A charger can be attached to the instrument for charging the batteries and providing a visual indication of charging status. The circuitry is designed to automatically turn off after a predetermined period of time in order to prevent undue battery drain. More specifically, when the push button switch 24 is depressed, a period of five seconds elapses before the measurement is frozen on the display 22. This is announced with a beep from a built in speaker. After thirty seconds has elapsed, the power to the circuitry is automatically turned off unless the switch 24 is depressed during this period.

Figure 2:
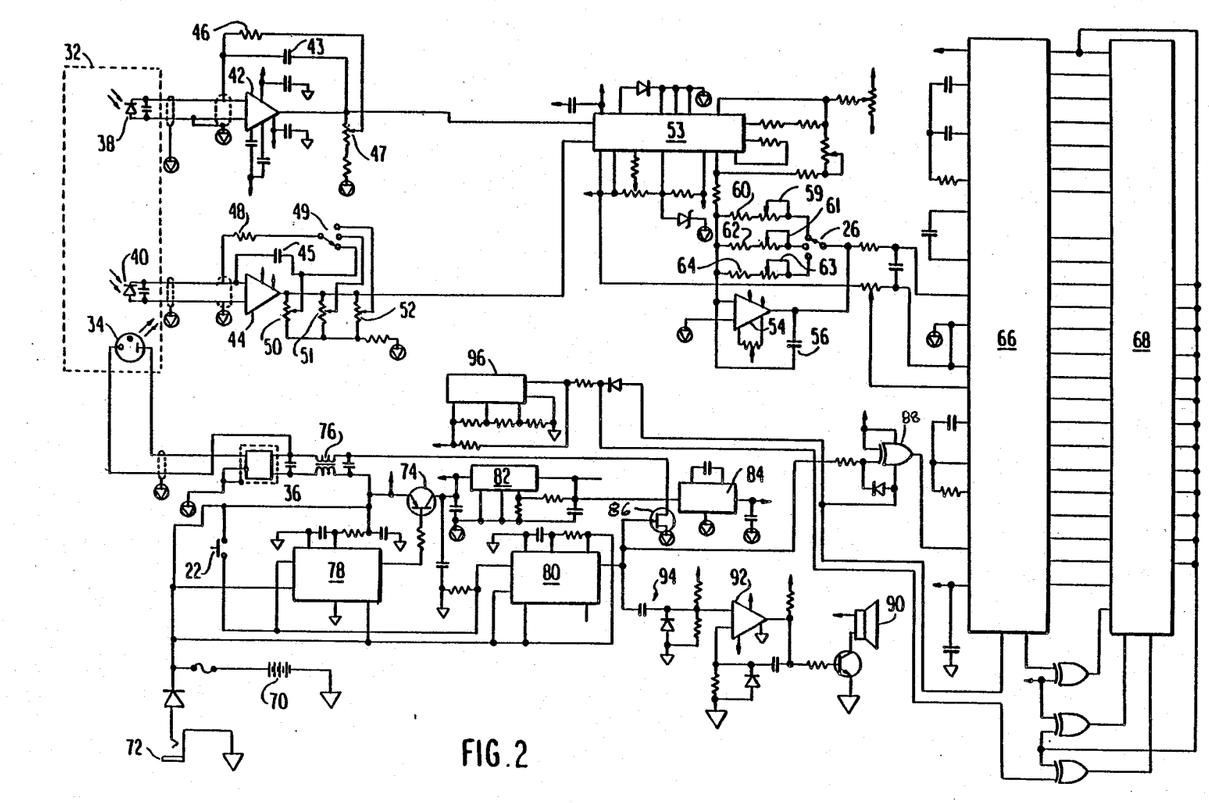
FIG. 2 is a block and schematic diagram of the electronic circuitry of the solution loading analyzer.

Turning now to FIG. 2, the dotted line 32 represents the probe head 16. It contains an ultraviolet fluorescent light source 34 connected via cable 20 to a power supply 36. Preferably, the light source 34 and power supply 36 are models BF959 and BF12V, respectively, manufactured by JKL Components Corporation of Pacoima, Calif. The probe head 32 also contains photodetectors 38 and 40 which are provided with ultraviolet filters (not shown) so as to be responsive to only preselected wavelengths of light from light source 34. The photodetectors 38 and 40 may be SD100-13-13-022 devices manufactured by the Silicon Detector Corporation of Newbury Park, Calif.

Photodetector 38 receives the light which is transmitted through the sample solution, while photodetector 40 measures the incident light from light source 34. The photodetectors 38 and 40 are connected across the input terminals of respective operational amplifiers 42 and 44. Both of these amplifiers have capacitive negative feedback provided by capacitors 43 and 45, respectively, as well as resistive negative feedback to provide the desired transfer function for amplification of the signals from photodetectors 38 and 40. The resistive feedback for amplifier 42 is provided by a resistor 46 and potentiometer 47; however, the resistive feedback for amplifier 44 is provided by a resistor 48 connected by a switch 49 connected to one of three potentiometers 50, 51, and 52. These potentiometers are used for the ZERO adjustment calibration of the instrument as described above.

The outputs of the operational amplifiers 42 and 44 are connected to inputs of a real time analog computational unit (ACU) 53. This is an AD538 integrated circuit (IC) device manufactured by Analog Devices, Inc., as described in their "Data Acquisition Databook Update and Selection Guide 1986". This device is a real-time computational circuit which provides precision analog multiplication, division, and exponentiation. Programming of the device is by pin strapping. The output voltage $V_o$ is proportional to $-\log_{10}(V_z/V_x)$, where $V_z$ is the voltage of the signal output by amplifier 42 and $V_x$ is the voltage of the signal output by amplifier 44.

The output of ACU 53 is connected to the input of operational amplifier 54 having both capacitive and resistive negative feedback. The capacitive feedback is provided by capacitor 56, while the resistive feedback is selectable by switch 26 to be either potentiometer/resistor combinations 59/60, 61/62 or 63/64. The SPAN potentiometers 59, 61, and 63 are used to calibrate the instrument for any of three different solutions as previously described.

The output of the operational amplifier 54 is supplied to the input of analog-to-digital (A/D) converter 66 which has a display hold feature. Preferably, the A/D converter 66 is an ICL7116 IC manufactured by the Intersil Corporation which is specially designed to drive an LCD display 68 and contains not only and A/D converter for converting analog voltage output of operational amplifier 54 to a digital value, but also the seven segment decoder/drivers required to drive the display 68.

Power to the circuitry is supplied by a battery 70 which is rechargeable via recharger (not shown) that is connected to the battery by means of jack 72. The positive terminal of battery 70 is connected to the emitter of NPN transistor 74 and also through the primary winding of transformer 76 to the d.c. input terminal of power supply 36. A pair of one-shots 78 and 80 are activated by pressing the push button switch 22. The first of these one-shots 78 has a thirty second time out period during which time transistor 74 is biased into conduction to supply battery voltage to series connected voltage regulators 82 and 84 supplying, respectively, regulated positive and negative voltages to the circuitry. At the end of the thirty second time-out period, the transistor 74 reverts to its nonconducting state turning off the power to voltage regulators 82 and 84.

The second one-shot 80 is powered from the collector of NPN transistor 74 and turns off after a five second delay. In doing so, the gate voltage to field effect transistor (FET) 86 is turned off so that the light source 34 is therefore energized only for a five second duration at the beginning of the thirty second time out period of one-shot 78. The output of one-shot 80 is also connected to one input of an exclusive OR gate 88, connected as an inverter, which actuates the hold feature of A/D converter 66. This causes the display to be frozen after five seconds, thus facilitating easy reading of the measurement. This is announced to the user by a beep produced by a speaker 90 which is connected to amplifier 92. The input of amplifier 92 is connected to an RC differentiator circuit 94 which produces a pulse output from the output of one-shot 80.

Connected across the battery and to the test output of A/D converter 66 is a low voltage sensing circuit 96. This circuit may be an ICL8212 IC manufactured by Intersil Corp., for example. If the battery charge falls below 10% of full charge, circuit 96 forces the output of display 68 to display a "LO BAT" indication, and the instrument cannot be used until the battery is recharged.

Figure 3:
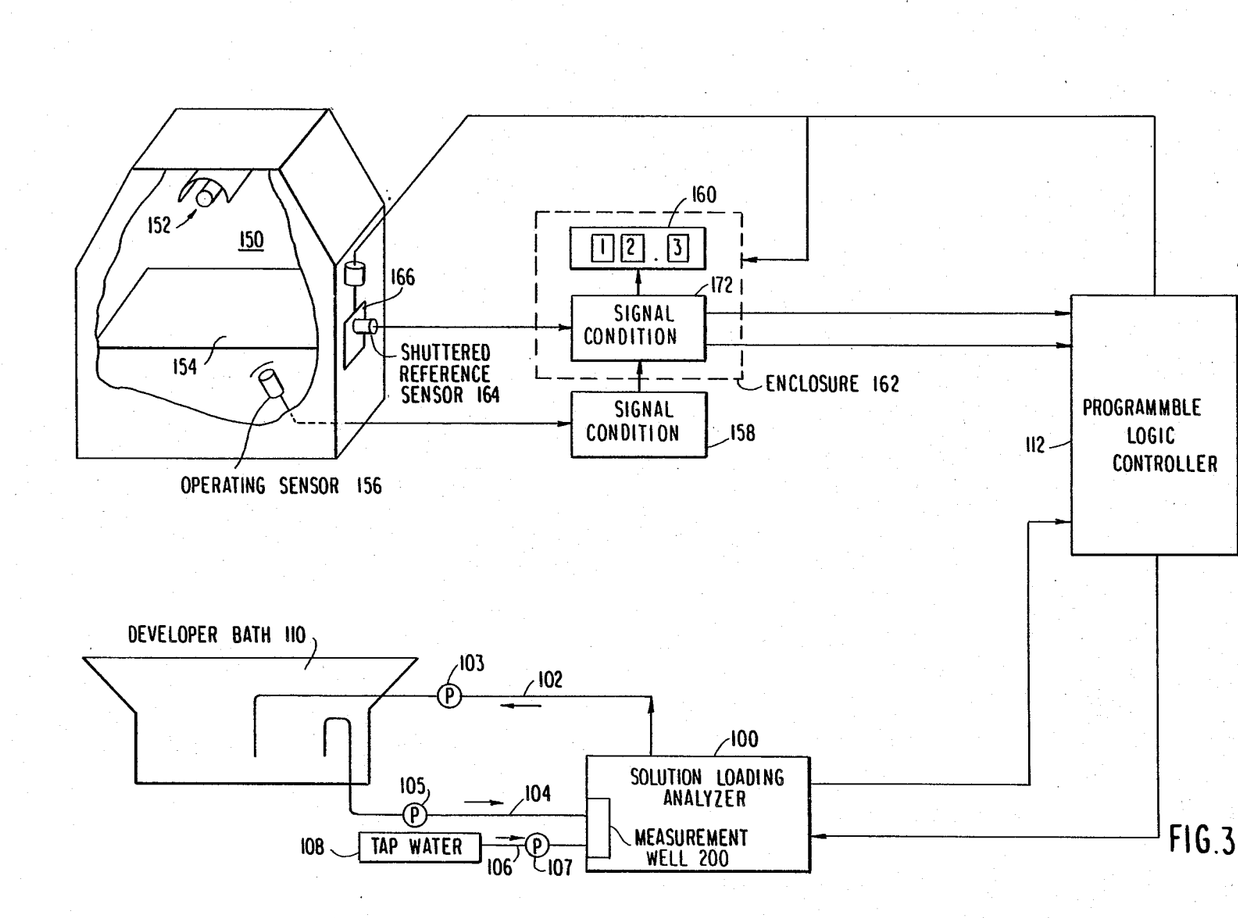
FIG. 3 is a block diagram of automated process monitoring instrumentation used to monitor the operation of an imager and the developer bath loading in a printed circuit printer.

FIG. 3 shows a solution loading analyzer 100, having a probe as described in conjunction with FIG. 1 and circuitry as described in conjunction with FIG. 2, implemented in a printed circuit board manufacturing environment where the percentage of photoresist material ("loading") in developer bath 110 is automatically monitored. It is to be understood that the arrangement shown in FIG. 3 is but one possible environment in which the solution loading analyzer 100 can be used and that other environments, e.g., waste water management, electroplating baths, fermenters, etc., are equally adaptable to automated process monitoring. Moreover, in the printed circuit board manufacturing environment itself, both the developer and the stripper baths can be monitored automatically with the programmable logic controller 112 keeping track of the loading in both baths. Only the developer bath 110 has been shown in FIG. 3 for the purposes of clarifying the operation of automated process monitoring. In addition, the circuitry of the solution loading analyzer 100 can be changed such that it is not battery powered. The battery power of the hand held model allows a technician to dip the probe head 16 into a solution to be tested and to freely walk to other solution vats and test them as well. In an automated process monitoring arrangement, the need for a technician is eliminated and, therefore, solution loading analyzer 100 does not require the freedom of movement attributable to battery power.

Samples of developer solution are obtained from bath 110 and analyzed by the solution loading analyzer 100 under the direction of a programmable logic controller 112. The programmable logic controller 112 can be an IPC 620 available from Honeywell, Inc. of Minnesota, a Modicon 984 available from the General Electric Corporation of New York, or any other suitable programmable logic controller. The programmable logic controller 112 is programmed to communicate with the solution loading analyzer 100, control the flow of fluids between the developer bath 110 and solution loading analyzer 100, and monitor the operation of the imager 150. The control of fluid flow in lines 102, 104, and 106, may be accomplished with commercially available pumps and valves.

Figure 4:
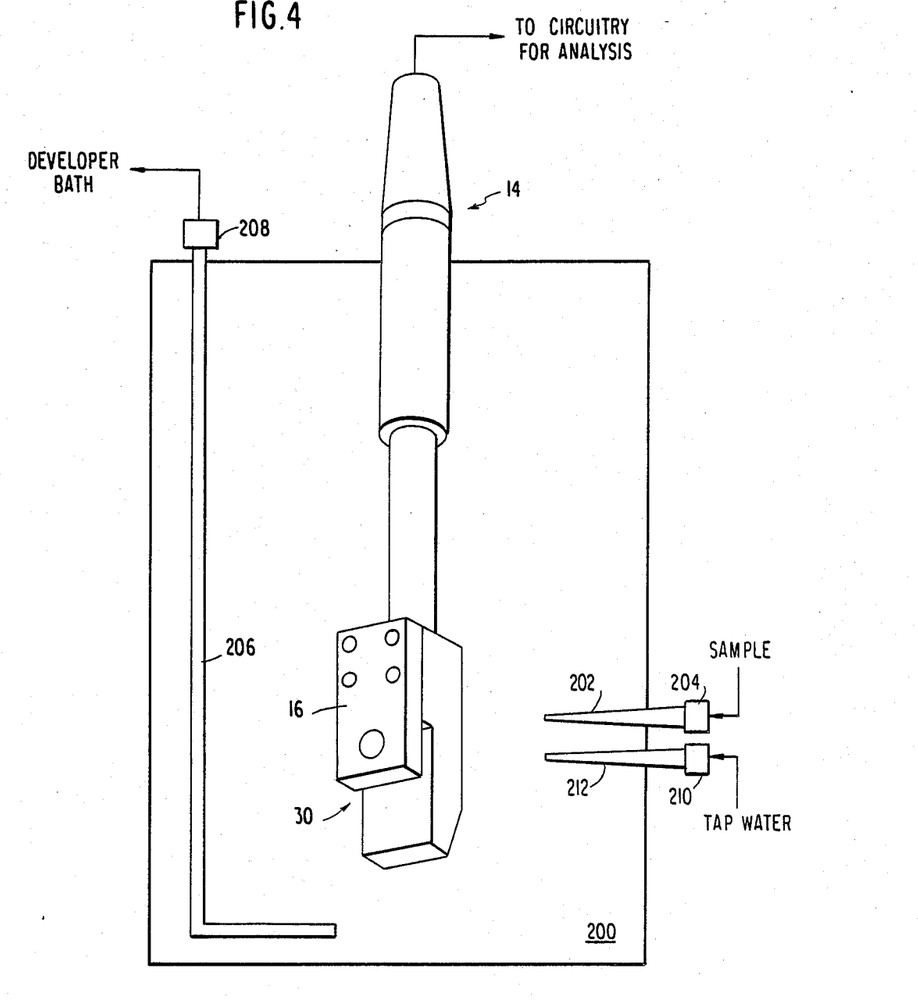
FIG. 4 is a block diagram of the inside of a measurement well present inside the solution loading analyzer showing an inverted probe head and the conduits used for moving the sample to and from the developer bath and a spray nozzle for cleaning the probe head.

FIG. 4 shows a probe 14 (FIG. 1) inserted in a measurement well 200 in the solution loading analyzer 100 (FIG. 3). Samples introduced into the measurement well 200 are measured in the same manner as described above using the circuitry in the solution loading analyzer 100 (FIG. 2).

Figure 5:
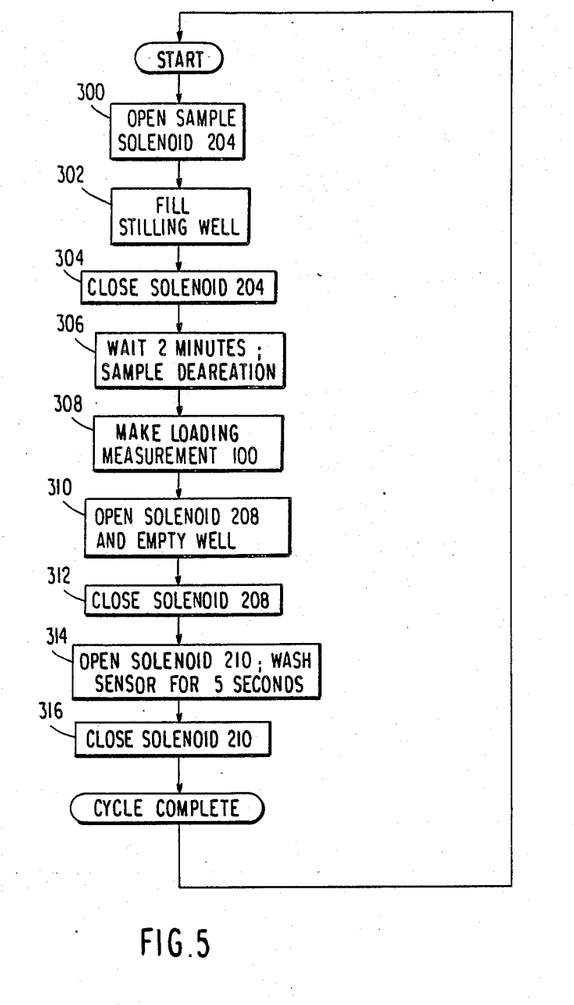
FIG. 5 is a flow chart of the process steps performed by the automated process monitoring instrumentation used to monitor the developer bath shown in FIG. 3.

FIG. 5 shows a flow chart of automated process monitoring procedures performed to monitor the loading in the developer bath 110 (FIG. 3).

The operation of the automated process monitor is best understood with reference to FIGS. 3, 4, and 5. In function block 300, the solenoid valve 204, connected to conduit 104, is opened to allow a sample from the developer bath 110 to be introduced into the measurement well 200. In function block 302, the measurement well 200 is filled with the sample through conduit 202. A pump 105 is used to transport the sample from the developer bath 110 to the solution loading analyzer 100. In function block 304, the solenoid valve 204 is closed after the measurement well 200 is filled by the sample. In function block 306, the sample developer solution is allowed to de-aerate for 1 to 2 minutes. Entrained air is known to produce artificially high readings; therefore, waiting for the sample to de-aerate before testing for absorbance allows for a more accurate measurement to be made.

In function block 308, the absorbance of the sample is measured. The measurement corresponds to the absorbance of the sample fluid located in channel 30 of probe 14. An analog voltage output directly proportional to solution loading is sent to the programmable logic controller 112 and converted to digital form. Simultaneously, the loading measurement is displayed on LCD 22 (FIG. 1) on the solution loading analyzer 100. Display of the solution loading at the solution loading analyzer 100 permits an operator to monitor solution loading, if desired. Results are accumulated at the programmable logic controller 112. It is to be understood that alternative light sensing elements can be used in place of probes 14 in sample well 200.

In function block 310, the developer sample is removed from the measurement well 200 through conduit 206 and returned to the developer bath 110 via conduit 102. Removal is accomplished by opening solenoid valve 208 and pumping the sample to the developer bath 110 with pump 103. In function block 312, the solenoid valve 208 is closed after the sample well has been evacuated.

In function block 314, the probe head 16 is cleaned by spraying a small jet of water or other suitable cleaning fluid on the probe head 16. Water is pumped from a source 108 under pressure by pump 107 through conduit 106 and solenoid valve 210 is opened for a short period of time, e.g., five seconds, to allow a stream of water to clean the probe head 16. Spray nozzle 212 is positioned in the measurement well 200 such that the stream of water will spray through the channel 30 in the probe head 16. Spray cleaning virtually eliminates the need for manual cleaning and requires no more than a pint of water. In function block 316, solenoid valve 210 is closed after cleaning probe head 16 is completed. The cleaning water can be removed from the measurement well 200 directly into a drain (not shown) because it contains very little photoresist. Alternatively, the water can be routed to the developer bath 110 via conduit 102, if desired. Solenoid operated valves 204, 208, and 210, and pumps 103, 105 and 107 operate under the direct control of the programmable logic controller 112.

Steps 300-316 constitute one complete cycle for automatically performing an absorbance measurement on the developer solution in bath 110. After the cycle is completed the process loops back around and starts over. The programmable logic controller 112 is programmed to perform the automatic absorbance measurement process shown in FIG. 5 at periodic timed intervals which are selected by the operator and are determined with regard to the type of fluid being monitored. For example, developer solution may require more or less frequent measurements than stripper solution in a printed circuit manufacturing process. Likewise, proper management of waste water may require measurements at completely different intervals from the intervals selected for printed circuit manufacturing.

With particular reference to printed circuit manufacturing, the programmable logic controller 112 can be programmed to test samples at any rate desired provided there is enough time to de-aerate the samples and clean the probe head 16. Feed and bleed replenishment as well as batch replacement can be performed automatically on the basis of measurements determined by the solution loading analyzer 100. In feed and bleed replenishment, the system is allowed to load to a preset level and then the developer solution is diluted with fresh solution to lower the loading to a preset lower loading level. In batch replacement, the loading level is monitored and the entire developer bath is replaced at one time.

Precalibration of the probe 14 is performed according to the same procedures described above. Zeroing is performed by inserting the probe head 16 in clear (unloaded) developer solution and adjusting a ZERO potentiometer in the solution loading analyzer until the numeric display 22 reads zero. Then the probe head 16 is inserted in a developer solution of known loading and the SPAN potentiometer is adjusted accordingly. Checking the calibration is required at only 1 to 2 month intervals. Note that other solutions with dissolved solids such as waste water or the industrial solutions found in electroplating baths, paper making vats, etc., can be measured using the automated process monitoring invention described above. All that is required is to precalibrate the solution loading analyzer 100 for the solution being measured and then to periodically sample and test the absorbance. The programmable logic controller 112 and the display 22 can be preset to display the units desired.

Figure 6:
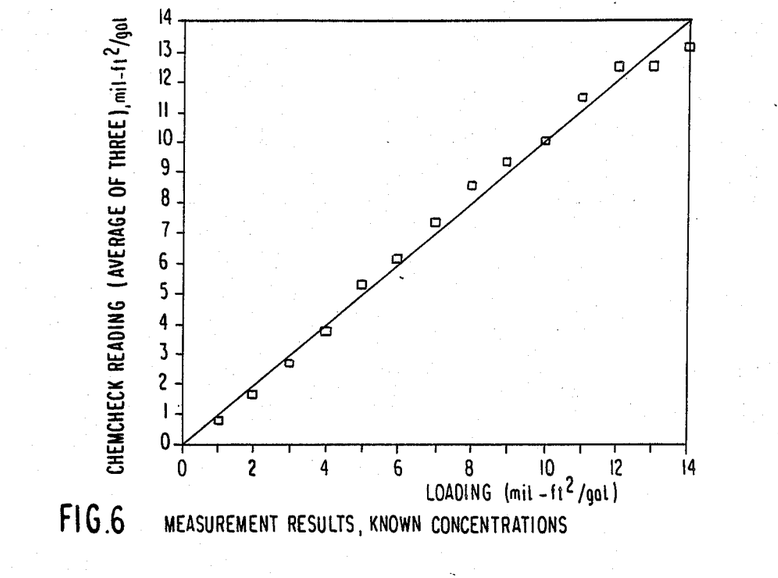
FIG. 6 is a graphical representation of measurement results obtained when panels with a known amount of photoresist were developed and the resulting loading was measured by the solution loading analyzer.

FIG. 6 shows the measurement results obtained when panels with a known amount of photoresist were developed and the resulting loading measured by the solution loading analyzer 100. Perfect correlation between the actual loading, along the abscissa, and measured loading, along the ordinate, would have produced a straight line at 45°. During this test run, dry film solder mask, one of the most difficult films to measure, was monitored using the solution loading analyzer.

Figure 7:
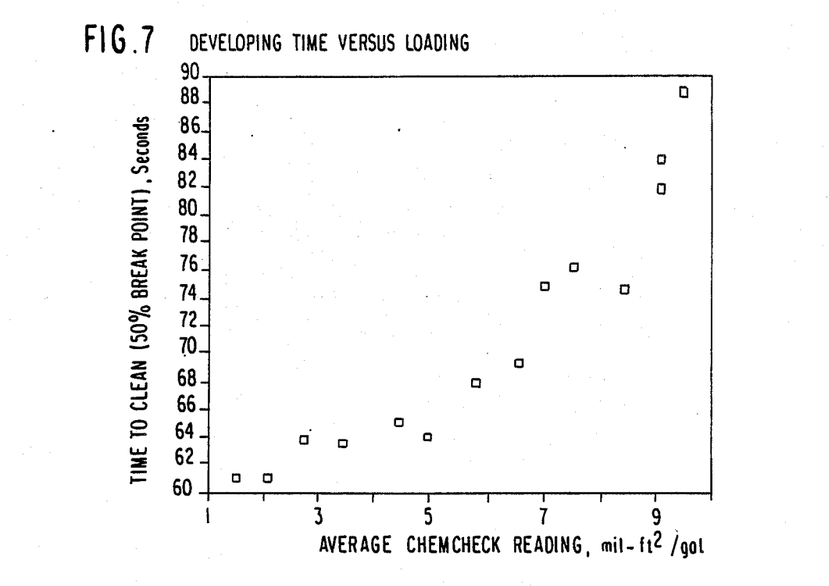
FIG. 7 is a graphical representation of development time versus loading.

FIG. 7 shows a plot of the development time versus loading. The graph shows increased loading produces relatively small increases in development time until a loading of about 8 mil-ft$^2$/gal. is reached. Development time then appears to increase rapidly. Although this relationship has not been unequivocally established, other tests appear to confirm a critical loading level. The significance of such a relationship is that production rates begin to deteriorate at a critical loading. If maximum throughput is to be obtained, loading should be kept at or below 8 mil-ft$^2$/gal.

Returning to FIG. 3, the programmable logic controller 112 may also be used for monitoring the imaging operation carried out in imager 150. An ultraviolet light 152 exposes a substrate 154 clad with photoresist. An operating sensor 156 measures the intensity of UV radiation emanating from lamp 152 and sends a corresponding signal to signal conditioner 158. The output from a UV sensor is a current proportional to UV intensity. The signal conditioner 158 converts the current into a voltage proportional to UV intensity. A digital display 160 on an enclosure 162 associated with the imager 150 displays the intensity of UV energy and allows an operator to adjust the intensity of lamp 152 for proper exposure or replace a defective lamp. The UV intensity information is also forwarded to the programmable logic controller 112 for automatic adjustment of lamp 152.

One aspect of the present invention is to provide for an automatic solarization check of the operating sensor 156. A reference sensor 164 is positioned behind a solenoid operated shutter 166. At predetermined intervals, the programmable logic controller 112 instructs the solenoid operated shutter to open, thus causing the reference sensor 164 to be exposed to the same intensity UV radiation as is the operating sensor 156. Since the reference sensor 164 is subject to relatively small amounts of UV radiation, its solarization should be very small and, therefore, its measurement should be accurate. The signals from both sensors, 156 and 164, are compared and when the sensor 156 has drifted a predetermined amount from sensor 164, an indication will be given to replace sensor 156. Because the probability of both sensors failing simultaneously is quite small, the probability of improper exposure due to undetected failure of the UV source is greatly decreased.

Figure 8:
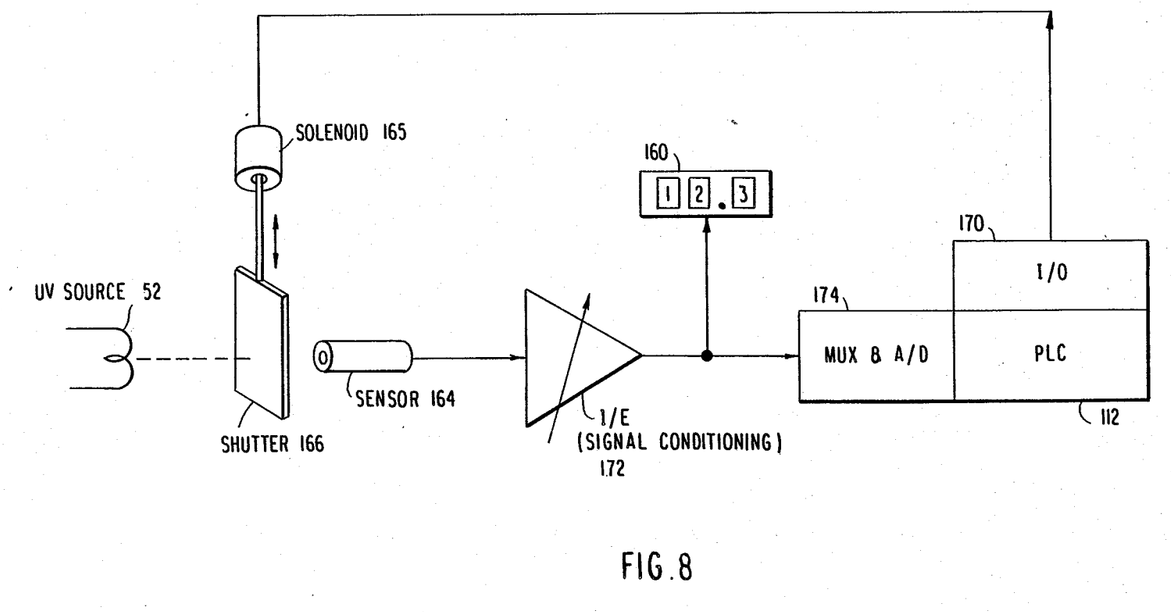
FIG. 8 is a block diagram of the UV sensor monitoring system.

FIG. 8 shows the programmable logic controller 112 controlling the opening and closing of shutter 166 via control signals being sent from an input/output (I/0) port 170 to solenoid 165. When the shutter 166 is opened, the full intensity of lamp 152 impinges on reference sensor 164. The signal conditioner 172 converts the current signal from the reference sensor 164, which is proportional to UV intensity, to a voltage signal which is proportional to UV intensity. The display 160 displays the intensity of lamp 152. A multiplexer and analog-to-digital converter 174 samples the voltage signal from the signal conditioner 172 and converts it to digital format for use by the programmable logic controller.

While the invention has been described in terms of the preferred embodiments, those skilled in the art will recognize that the invention can be practiced with modification within the spirit and scope of the appended claims.

Having thus described our invention, what we claim as novel and desire to secure by Letters Patent is as follows:

1. Instrumentation for measuring solution loading; comprising:
a probe with a light source and first and second photodetectors positioned in a measurement head section of said probe, said probe being of ruggedized construction for resisting the effects of caustic solutions and mechanical shock, said light source and said first photodetector being positioned on opposite sides of a channel in said measurement head with said first photodetector receiving transmitted light transmitted through a solution positioned in said channel, said second photodetector receiving incident light direct from said light source; and a hand held housing connected to said probe by a flexible cable, said hand held housing including
  (i) a computation means, said computation means connected to receive first and second signals indicative of said transmitted light and said incident light, respectively, from said first and second photodetectors for computing a negative logarithm of the radio of said first and second signals, said computation means outputting a third signal indicative of said negative logarithm;
  (ii) a display mans, said display means connected to said computation means and responsive to said third signal for displaying a value proportional to said output signal, said value being presented in appropriate units chosen by an operator;
  (iii) first and second operational amplifiers respectively connected between said first and second photodetectors and said computation means for amplifying said first and second signals generated by said first and second photodetectors;
  (iv) first and second resistive feedback means respectively connected across said first and second operational amplifier for providing a zero adjustment calibration for said instrumentation;
  (v) a third operational amplifier connected between said computation means and said display means for amplifying said third signal output from said computation means;
  (vi) a third resistive feedback means connected across said third operational amplifier for providing a span adjustment calibration for said instrumentation; and
  (vii) a battery and control means responsive to a switch for supplying battery power to said light source and said first and second photodetectors, said computation means, and said display means for a first predetermined period of time, said control means terminating the supply of battery power to said light source and said first and second photodetectors after a second predetermined period of time and freezing a display on said display means, said second predetermined period of time being of shorter duration than said first predetermined period of time, said computation means terminating battery power to said computation means and said display means at the expiration of said first predetermined period of time.

2. Instrumentation as recited in claim 1 wherein said control means comprises first and second one shots activated simultaneously, said first one shot having a delay period equal to said first predetermined period of time, and said second one shot having a delay period equal to said second predetermined period of time.

3. Instrumentation as recited in claim 1 further comprising audible means activated by said control means at the expiration of said second predetermined period of time for sounding an indication that a measurement may be read from said display means.

4. Instrumentation as recited in claim 1 wherein said housing includes a handle which may be grasped by one hand of a user while the other hand of the user is used to hold said hand held probe means, said switch being located on said housing adjacent said handle and operable by a finger of the hand used to grasp said handle.

5. Instrumentation as recited in claim 1, further comprising:
  a measurement well for containing said sample of said solution, said probe being positioned inside said measurement well;
  flow pathway means connected to said measurement well for transporting said sample to and from said measurement well;
  cleaning means connected to said measurement well having a spray nozzle positioned inside said measurement well for cleaning said probe; and
  a programmable logic controller connected to said probe, said flow pathway means, and said cleaning means for controlling flow in said flow pathway means, for controlling measurement by said probe, and for controlling cleaning by said cleaning means, said programmable logic controller providing timed directions to transport said sample to said measurement well through said flow pathway means, to permit said sample to de-aerate in said measurement well, to measure said sample for solution loading with said probe, to transport said sample away from said measurement well, and to clean said probe by spraying cleaning fluid on said probe through said spray nozzle.

6. Instrumentation as recited in claim 5 wherein said flow pathway means comprises first and second conduits, each conduit having a first end opening into said measurement well, each conduit having a second end opening into a vat of solution from which said sample is taken, said first conduit for transporting said sample from said vat to said measurement well, said second conduit for transporting said sample from said measurement well to said vat.

7. Instrumentation as recited in claim 6 further comprising first and second solenoid actuated valves in said first and second conduits, respectively, said programmable logic controller being electrically connected to said first and second solenoid actuated valves for signalling the opening and closing of said first and second solenoid actuated valves for controlling the flow of said sample to and from said measurement well.

8. Instrumentation as recited in claim 5 wherein said cleaning means comprises a conduit connecting said spray nozzle to a source of said cleaning fluid and a solenoid actuated valve positioned in said conduit and electrically connected to said programmable logic controller, said programmable logic controller controlling the opening and closing of said solenoid actuated valve and allowing for the cleaning of said probe between samples.

9. Instrumentation as recited in claim 5 wherein said programmable logic controller accumulates output signal data from said computation means and determines whether a vat of solution from which said sample is withdrawn should be replenished.

10. Instrumentation as recited in claim 5 wherein said programmable logic controller accumulates output signal data from said computation means and determines whether a vat of solution from which said sample is withdrawn should be replaced.

11. Instrumentation for automated process monitoring of the amount of material in a liquid solution, comprising:
a solution loading analyzer including a measurement well for containing a sample of solution to be analyzed, probe means positioned inside said measurement well and including light source means for generating light radiation and first and second photodetector means for receiving, respectively, light transmitted through said sample and incident light from said light source means, a computation means connected to receive signals respectively from said first and second photodetector means for computing the negative logarithm of the ratio of said signals and generating an output signal;
flow pathway means connected to said solution loading analyzer for transporting said sample to and from said measurement well;
cleaning means connected to said solution loading analyzer having a spray nozzle positioned inside said measurement well for cleaning said probe means between samples; and
a programmable logic controller connected to said solution loading analyzer, said flow pathway means, and said cleaning means for controlling flow in said flow pathway means, for controlling measurement by said probe means, and for controlling cleaning by said cleaning means, said programmable logic controller providing timed directions to transport said sample to said measurement well in said solution loading analyzer through said flow pathway means, to permit said sample to de-aerate in said measurement well, to measure said sample for solution loading with said probe means, to transport said sample away from said measurement well, and to clean said probe means by spraying cleaning fluid on said probe means through said spray nozzle.

12. The instrumentation for automated process monitoring as recited in claim 11 wherein said flow pathway means comprises first and second conduits, each conduit having a first end opening into said measurement well in said solution loading analyzer, each conduit having a second end opening into a vat of solution from which said sample of solution to be analyzed is taken, said first conduit for transporting said sample from said vat to said measurement well, said second conduit for transporting said sample from said measurement well to said vat.

13. The instrumentation for automated process monitoring as recited in claim 12 further comprising first and second solenoid actuated valves in said first and second conduits, respectively, said programmable logic controller being electrically connected to said first and second solenoid actuated valves for signalling the opening and closing of said first and second solenoid actuated valves for controlling the flow of said sample to and from said measurement well.

14. The instrumentation for automated process monitoring as recited in claim 11 wherein said cleaning means comprises a conduit connecting said spray nozzle to a source of said cleaning fluid and a solenoid actuated valve positioned in said conduit and electrically connected to said programmable logic controller, said programmable logic controller controlling the opening and closing of said solenoid actuated valve and allowing for the cleaning of said probe means between samples.

15. The instrumentation for automated process monitoring as recited in claim 11 wherein said programmable logic controller accumulates output signal data from said computation means in said solution loading analyzer and determines whether a vat of solution from which said sample is withdrawn should be replenished.

16. The instrumentation for automated process monitoring as recited in claim 11 wherein said programmable logic controller accumulates output signal data from said computation means in said solution loading analyzer and determines whether a vat of solution from which said sample is withdrawn should be replaced.

17. The instrumentation for automated process monitoring as recited in claim 11 further comprising a display means connected to said computation means in said solution loading analyzer and responsive to said output signal for displaying a value proportional to said output signal.

18. The instrumentation for automated process monitoring as recited in claim 17 further comprising selectable gain means including a switch means connected between said computation means and said display means in said solution loading analyzer for permitting the selection of a plurality of precalibrated gains corresponding to a plurality of different solutions from which samples will be drawn.

19. The instrumentation for automated process monitoring as recited in claim 18 further comprising first and second amplifier means connected, respectively, between said first and second photodetector means and said computation means in said solution loading analyzer for amplifying the signals generated by said first and second photodetector means, said first and second amplifier means including calibration means for providing a zero adjustment of said solution loading analyzer for each of said selectable gains.

20. Instrumentation for the automated process monitoring of an imager and a developer bath in a printed circuit printer, comprising:
operating and reference ultraviolet sensors positioned in an imager for exposing photoresist film layered on a substrate, said operating sensor being continuously exposed to ultraviolet radiation from an ultraviolet lamp in said imager, said reference ultraviolet sensor being protected from continuous exposure by a solenoid actuated shutter;
a developer bath for developing exposed photoresist film on a substrate connected to a solution loading analyzer by a flow pathway means, said solution loading analyzer being supplied samples of developer solution via said flow pathway means;
said solution loading analyzer including a measurement well for containing a sample of said developer solution, probe means positioned inside said measurement well and including light source means for generating light radiation and first and second photodetector means for receiving, respectively, light transmitted through said sample and incident light from said light source means, a computation means connected to receive signals respectively from said first and second photodetector means for computing the negative logarithm of the ratio of said signals and generating an output signal; and
a programmable logic controller electrically connected to receive signals proportional to ultraviolet radiation sensed by said operating and reference ultraviolet sensors, to said solenoid actuated shutter, and to said solution loading analyzer for monitoring the solarization of said operating sensor and the loading of said developer bath, said programmable logic controller being programmed to test the solarization of said operating sensor by directing said solenoid actuated shutter to open at a predetermined time and expose said operating and reference sensors to the same intensity ultraviolet radiation and comparing the signals proportional to the ultraviolet radiation sensed by said operating and reference sensors, said programmable logic controller being programmed to determine loading of said developer bath by monitoring said output signal from said computation means of said solution loading analyzer.

* * * * *